United States Patent [19]

Fujita

[11] Patent Number: 4,650,904
[45] Date of Patent: Mar. 17, 1987

[54] PROCESS FOR PRODUCING MIXED TERTIARY AMINE OXIDE

[75] Inventor: Koichi Fujita, Matsuzaka, Japan

[73] Assignee: Mitsubishi Petrochemical Company, Limited, Tokyo, Japan

[21] Appl. No.: 676,807

[22] Filed: Nov. 30, 1984

[30] Foreign Application Priority Data

Dec. 1, 1983 [JP] Japan .............................. 58-227549

[51] Int. Cl.$^4$ ............................................. C07C 135/02
[52] U.S. Cl. ..................................... 564/298; 564/297
[58] Field of Search ......................... 564/298, 258, 257

[56] References Cited

U.S. PATENT DOCUMENTS

| | | | |
|---|---|---|---|
| 3,215,741 | 11/1965 | Chadwick | 564/298 |
| 3,275,673 | 9/1966 | Barlow | 564/298 X |
| 3,283,007 | 11/1966 | Chadwick | 564/298 |
| 3,336,387 | 8/1967 | Finch et al. | 564/297 |
| 3,463,817 | 8/1969 | Maknken | 564/298 |
| 4,247,480 | 1/1981 | Murata et al. | 564/298 |

Primary Examiner—Robert V. Hines
Attorney, Agent, or Firm—Oblon, Fisher, Spivak, McClelland & Maier

[57] ABSTRACT

A process for producing an aqueous solution of a straight-chain alkyl tertiary amine oxide and a branched-chain alkyl tertiary amine oxide by reacting aliphatic tertiary amines with an aqueous solution of hydrogen peroxide is disclosed. In this process, a tertiary amine which mainly consists of a branched-chain tertiary amine is first reacted with excess hydrogen peroxide, and then, a straight-chain alkyl tertiary amine which is substantially free of a branched-chain alkyl group is added to the reaction mixture for permitting further reaction with hydrogen peroxide. The process achieves a high overall conversion of the starting amines, and the final product has an extremely low level of residual hydrogen peroxide.

4 Claims, No Drawings

PROCESS FOR PRODUCING MIXED TERTIARY AMINE OXIDE

BACKGROUND OF THE INVENTION

1. Field of the Invention

The present invention relates to a process for producing an aqueous solution of a mixture of a straight-chain alkyl tertiary amine oxide and a branched-chain alkyl tertiary amine oxide by reacting aliphatic tertiary amines with an aqueous solution of hydrogen peroxide.

2. Prior Art

Aliphatic tertiary amine oxides are effective surface active agents and are extensively incorporated in shampoos and dish detergents so as to formulate liquid detergents that have mild effects on the hand. However, amine oxides suitable for use in this application must have a minimum content of unreacted amines. The presence of large quantities of unreacted amines not only reduces the cleaning effect of the amine oxides but also causes undesired effect on the color, smell and skin irritating property of the final product. Therefore, at least 99 mol % conversion is necessary for producing commercially acceptable amine oxides by reacting tertiary amines with hydrogen peroxide.

A common practice for reducing the residual amount of unreacted amines is by reacting amines with excess hydrogen peroxide. However, the amine oxide that can be incorporated in liquid detergents for home use should preferably be free of residual hydrogen peroxide, and after completion of the reaction, the residual hydrogen peroxide must be decomposed to a level of 0.1 wt % or less. However, oxygen gas evolving during the decomposition of hydrogen peroxide causes extensive bubbling of the aqueous amine oxide solution, and this prevents the smooth progress of the decomposition reaction.

Several methods have been proposed for producing amine oxides by using a small excess of hydrogen peroxide so as to reduce the residual hydrogen peroxide level to 0.1 wt % or below and to achieve at least 99 mol % conversion of the amine. According to Japanese Patent Publication No. 14089/1966, the amine is reacted with hydrogen peroxide in the presence of a chelating agent that is selected from among diethylenetriamine pentaacetic acid, ammonium salts and alkali metal salts thereof. Japanese Patent Publication No. 11042/1967 shows a method wherein sodium pyrophosphate and sodium bicarbonate are simultaneously added to the reaction system. Japanese Patent Application (OPI) No. 54160/1982 (the symbol OPI as used herein means an unexamined published Japanese patent application) proposes performing the reaction in the presence of a polybasic acid having one or more hydroxyl groups, or a salt of such polybasic acid.

Detergents comprising a mixture of a tertiary amine oxide having a long, straight-chain alkyl group and tertiary amine oxide having a long, branched-chain alkyl group are known to be superior to the detergents containing above described aliphatic tertiary amine oxide with respect to the non-skin irritating effect, stability at low temperature, solubilizability and detergency (see Japanese Patent Publication No. 19526/1966, Japanese Patent Application (OPI) Nos. 141400/1981 and 139200/1982)).

The mixed tertiary amine which provides a mixture of branched-chain alkyl tertiary amine oxide and straight-chain alkyl tertiary amine oxide may be prepared by the following process: first, a higher alcohol containing a mixture of branched-chain and straight-chain alkyls that is synthesized by the oxo process is converted to a mixed alkyl chloride, which is then aminated with a lower dialkylamine. Alternatively, as shown in Japanese Patent Application (OPI) No. 105945/1983, a long-chain olefin may be reacted with a lower dialkylamine in the presence of a gaseous mixture of hydrogen and carbon monoxide. The mixed tertiary amines produced by these methods have a straight chain content in the range of 40 to 80 wt %.

One may assume that in producing an amine oxide by oxidizing the mixture of branched-chain and straight-chain alkyl tertiary amines with hydrogen peroxide, the level of residual hydrogen peroxide could be reduced to 0.1 wt % or less whereas the conversion of the mixed amine be increased to 99 mol % or higher by direct application of one of the methods that are described above in connection with the production of the aliphatic tertiary amine oxide. As it turned out, however, these objects were very difficult to attain. The rate of reaction of the branched-chain alkyl tertiary amine is much slower than that of the straight-chain alkyl tertiary amine, and even if the conversion of the straight-chain alkyl tertiary amine has reached 100%, much of the branched-chain alkyl tertiary amine remains unreacted. In order to enhance the conversion of the branched-chain alkyl tertiary amine, an excess amount of hydrogen peroxide must be used, but then, the other object, i.e., reduced level of residual hydrogen peroxide, cannot be obtained.

SUMMARY OF THE INVENTION

According to the present invention, the mixture of straight- and branched-chain alkyl tertiary amines can be oxidized with hydrogen peroxide in such a manner that an amine conversion of 99 mol % or higher is achieved within a fairly short period of time while the level of residual hydrogen peroxide is reduced to 0.1 wt % or below. More specifically, the present invention provides a process for producing an aqueous solution of a mixture of a straight-chain alkyl tertiary amine oxide and a branched-chain alkyl tertiary amine oxide by reacting aliphatic tertiary amines with an aqueous solution of hydrogen peroxide. This process is characterized by two steps, wherein a tertiary amine mainly consisting of a branched-chain alkyl tertiary amine is reacted with excess hydrogen peroxide, and then, a straight-chain alkyl tertiary amine which is substantially free of a branched-chain alkyl group is added to the reaction mixture for permitting further reaction with hydrogen peroxide.

DETAILED DESCRIPTION OF THE INVENTION

The long-chain alkyl tertiary amines used as starting amine materials in the process of the present invention consist of straight-chain and branched-chain alkyl amines. The former is an aliphatic tertiary amine of the formula:

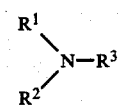

(wherein $R^1$ and $R^2$ independently represent methyl or ethyl group; $R^3$ is a straight-chain alkyl group having 8~18 carbon atoms). The other amine, or the branched-chain alkyl amine, is an aliphatic tertiary amine of the formula:

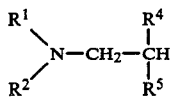

(wherein $R^1$ and $R^2$ independently represent methyl or ethyl group; $R^4$ and $R^5$ are each a straight-chain alkyl group, provided that the total number of carbon atoms in $R^4$ and $R^5$ is 6~16).

The process of the present invention may proceed as follows. First, a tertiary amine which mainly consists of the branched-chain alkyl tertiary amine is oxidized with excess hydrogen peroxide; then, the more reactive straight-chain alkyl tertiary amine is added and reacted with hydrogen peroxide that may be supplemented with an additional amount of $H_2O_2$. By this procedure, an aqueous solution of mixed tertiary amine oxide can be produced, and the so obtained solution has a residual hydrogen peroxide level of 0.1 wt % or less and an overall amine conversion of 99 mol % or more.

The induction period of the reactions occurring in the method of the present invention may be shortened by using the starting tertiary amines in a fine dispersion phase. An advantageous method for preparing the desired fine dispersion in water is to oxidize the branched-chain alkyl tertiary amine in the first step in the presence of an amine oxide that is added in an amount of 5~10 wt % of the amine. Although the composition of the amine oxide added in the first step is not critical, it preferably has alkyl groups and straight chains whose carbon number and linearity are the same as those of the final amine oxide producid in the subsequent oxidation reaction. The long-chain alkyl groups in the additional amine oxide may comprise straight chains or branched chains or both. The linearity of the intented amine oxide may be controlled by varying the amount of the straight-chain alkyl tertiary amine that is substantially free of branched-chain alkyl groups and which is added to the reaction system after the oxidation of the previously added branched-chain alkyl tertiary amine.

Instead of adding an amine oxide, a mixture of a branched-chain alkyl tertiary amine with 15 wt % or more, preferably 15~40 wt % of a straight-chain alkyl tertiary amine may be used. The straight-chain alkyl amine in this mixture is reacted with hydrogen peroxide prior to the branched-chain alkyl tertiary amine, and the resulting amine oxide will act as an agent to disperse the branched-chain amine.

The starting tertiary amines used in the present invention may be a mixture of branched-chain and straight-chain alkyl tertiary amines that are typically synthesized by the oxo process. Having different boiling points, the two types of tertiary amines can be separated fractional distillation. In this case, the branched-chain alkyl tertiary amine fraction may contain 15~40 wt %, or sometimes a greater amount, of the straight-chain alkyl tertiary amine fraction, which should preferably not contain more than 1 wt % of the branched-chain alkyl tertiary amine.

In the oxidation of the branched-chain alkyl tertiary amine, hydrogen peroxide must be used in an excess amount so that at least 1 wt % of residual hydrogen peroxide is present after completion of the first stage reaction. This is effective for promoting the oxidation of the branched-chain alkyl tertiary amine.

In order to provide a higher conversion of amines, the oxidation with hydrogen peroxide may be effected in the presence of various reaction promoters, such as a chelating agent made of ethylenetriamine pentaacetic acid or its ammonium or alkali metal salt (Japanese Patent Publication No. 14089/1966), a combination of pyrophosphate salt and sodium bicarbonate (Japanese Patent Publication No. 11042/1967), and a polybasic acid having one or more hydroxyl groups or a salt thereof as shown in Japanese Patent Application (OPI) No. 54160/1982.

After the oxidation of the branched-chain alkyl tertiary amine has been substantially completed, a straight-chain alkyl tertiary amine which is substantially free of branched-chain alkyl groups is added to the reaction system. The straight-chain alkyl tertiary amine must be added in an amount which is at least sufficient to react with excess hydrogen peroxide that is present at the time when the first-stage oxidation of the branched-chain alkyl tertiary amine has been completed. By satisfying this requirement, it is possible to obtain an overall amine conversion of at least 99 mol % and a residual hydrogen peroxide level of 0.1 wt % or less in the final reaction product.

As already mentioned, the linearity of alkyl chains in the intended amine oxide can be controlled by varying the amount of the straight-chain alkyl tertiary amine that is added in the second oxidation step. If necessary, an additional amount of hydrogent peroxide may be supplied to the reaction system before or during the oxidation of the straight-chain alkyl tertiary amine.

According to the method of the present invention, an aqueous solution of hydrogen peroxide is used in an excess amount with a view to obtaining an amine conversion of 99 mol % or more in the oxidation of the branched-chain alkyl tertiary amine; furthermore, the straight-chain alkyl tertiary amine is added in the second step for the purpose of consuming the excess hydrogen peroxide so as to reduce the level of residual hydrogen peroxide in the final product to 0.1 wt % or below. Therefore, if one wants to obtain an amine oxide having the linearity within the predetermined range, care must be taken so that the amount of the straight-chain alkyl tertiary amine which is present either in the branched-chain alkyl tertiary amine to be oxidized in the first step or in the amine oxide added in the first oxidation step, is properly selected in consideration of the amount of the straight-chain alkyl tertiary amine to be added in the subsequent oxidation step. The excess hydrogen peroxide used in the oxidation of the branched-chain alkyl tertiary amine must not exceed the necessary amount for accomplishing the oxidation of the straight-chain alkyl tertiary amine that is subsequently added to the reaction system.

The straight-chain alkyl tertiary amine is oxidized very rapidly with hydrogen peroxide. After the oxidation of the branched-chain alkyl tertiary amine, residual hydrogen peroxide whose amount can be determined from the residual content of hydrogen peroxide is reacted with the corresponding amount of the straight-chain alkyl tertiary amine.

An additional amount of hydrogen peroxide may be used as required. By this procedure, the desired final amine oxide having a residual hydrogen peroxide concentration of 0.1 wt % or less can be obtained.

During the reaction which occurs in the process of the present invention, a sample may be taken out of the reaction mixture for measuring the concentrations of the unreacted amines and hydrogen peroxide. If necessary, an aqueous solution of hydrogen peroxide may be added to the reaction mixture. These sampling and analytic procedures are effective for the purpose of ensuring a thorough and rapid completion of the reaction.

The advantages of the present invention are hereunder described in greater detail by reference to working and comparative examples, but it should be understood that the scope of the invention is by no means limited to the working examples shown below.

COMPARATIVE EXAMPLE 1

A glass reaction vessel was charged with 91 g of N,N-dimethyl-tridecylamine (linearity: 69.4 wt %), 25.6 g of water, 0.28 g of sodium bicarbonate and 0.28 g of sodium pyrophosphate decahydrate. The N,N-dimethyltridecylamine had been synthesized from 1-dodecene, dimethylamine and a mixed gas of hydrogen and carbon monoxide. While the mixture was held at 80° C. under stirring, 195 g of 9 wt % aqueous hydrogen peroxide was added dropwise over a period of 3 hrs. After completion of the addition, the reaction was continued for another 4 hours at 80° C. Part of the reaction mixture was sampled at given intervals, and the sum of the amounts of unreacted amine and the product amine oxide was measured by titration with hydrochloric acid. The unreacted amine was extracted into an n-hexane phase with a liquid mixture of n-hexane, methanol and water. The conversion of branched- and straight-chain amines were determined by gas chromatographic analysis of the n-hexane phase. The level of the residual hydrogen peroxide was determined by titration with potassium permanganate.

As a result of the 4-hr reaction following the dropwise addition of aqueous hydrogen peroxide, the overall amine conversion reached 99.3 mol %. However, the level of residual hydrogen peroxide was 1.1 wt %.

The profile of the conversion of the straight chain and branched-chain alkyl tertiary amines, as well as the profile of the level of residual hydrogen peroxide are summarized in Table 1, from which one can see that the branched-chain alkyl tertiary amine was oxidized much more slowly than the straight-chain alkyl tertiary amine.

TABLE 1

| Reaction time (hr.) | $H_2O_2$ | Amine conversion (mol %) straight-chain amine | branched-chain amine | total amine | Concentration of residual $H_2O_2$ (wt %) |
|---|---|---|---|---|---|
| 1 | added | 33.6 | 6.3 | 25.2 | 1.33 |
| 2 | drop- | 88.7 | 31.1 | 71.1 | 0.82 |
| 3 | wise | 99.7 | 60.0 | 87.6 | 1.72 |
| 5 | None | 100 | 88.9 | 96.6 | 1.15 |
| 7 |  | 100 | 97.6 | 99.3 | 1.10 |

COMPARATIVE EXAMPLE 2

The procedure of Comparative Example 1 was repeated except that 7.67 wt %, rather than 9 wt %, hydrogen peroxide was added dropwise to the reaction mixture. As a result of 4-hr reaction following the addition of $H_2O_2$, all of the straight-chain amine was converted to an amine oxide. However, the conversion of the branched-chain amine was 80.6 mol %, and the overall amine conversion was 94.1 mol %. The concentration of residual hydrogen peroxide in the product amine oxide was 0.42 wt %. The reaction was further continued and 26 hours after the dropwise addition of $H_2O_2$, the overall amine conversion reached 99.1 mol % and the concentration of residual hydrogen peroxide was 0.12 wt %.

COMPARATIVE EXAMPLE 3

A glass reaction vessel was charged with 91 g of the dimethyl-tridecylamine used in Comparative Example 1, 190.4 g of water and 0.42 g of citric acid. While the mixture was held at 80° C. under agitation, 42.5 g of 33.2 wt % aqueous hydrogen peroxide was added dropwise over a period of 3 hours. Following the completion of the addition of $H_2O_2$, the reaction was continued for another 20 hours at 80° C. The overall amine conversion was 99.4 mol %, and the concentration of residual hydrogen peroxide was 0.31 wt %.

EXAMPLE 1

A distillation column (ID: 4 cm) having 20 theoretical trays was charged with dimethyltridecylamine that had been synthesized from 1-dodecene, dimethylamine and a mixed gas of hydrogen and carbon monoxide. Distillation was conducted at 10 mmHg to obtain fraction No. 1 that was principally composed of a branched-chain amine (bp. 137.5°~146.5° C.) and fraction No. 2 that was mainly composed of a straight-chain amine (bp. 146.5° C.). Fraction No.1 contained 25 wt % of the straight-chain amine, and fraction No. 2 contained 99.5 wt % of the straight-chain amine.

A glass reaction vessel was charged with 53.7 g of Fraction No. 1, 25.6 g of water, 0.16 g of sodium bicarbonate, 0.16 g of sodium pyrophosphate decahydrate and 45 g of the aqueous amine oxide solution prepared in Comparative Example 2 (oxide content: 30.9 wt %). While the mixture was held at 80° C. under agitation, 56 g of 9.3 wt % aqueous hydrogen peroxide was added dropwise to the mixture over a period of 1.5 hours, followed by the dropwise addition of another 56 g of 9.3 wt % aqueous $H_2O_2$ over a period of 3 hours. After the completion of the addition of $H_2O_2$, the reaction was continued for another 6 hours at 80° C. On the third hour of the continued reaction, 7.7 g of 35 wt % aqueous $H_2O_2$ was added to the mixture. The conversion of the straight-chain amine was 100%, whereas that of the branched-chain amine was 99.8 mol %. The concentration of residual hydrogen peroxide was 2.12 wt %.

Subsequently, a mixture of Fraction No. 2 (37.3 g), 35 wt % aqueous hydrogen peroxide (1.9 g), water (70.7 g), sodium bicarbonate (0.12 g) and sodium pyrophosphate decahydrate (0.12 g) was charged into the reaction vessel, and the second-stage reaction was conducted at 80° C. for 6 hours. The overall conversion of the amines added in the first and second stages of the reaction had reached 99.2 mol %, whereas the level of residual hydrogen peroxide was 0.086 wt %.

EXAMPLE 2

N,N-Dimethylundecylamine was synthesized from 1-decene, dimethylamine and a gas mixture of hydrogen and carbon monoxide. This amine was distilled as in Example 1 to obtain fraction No. 1 mainly consisting of a branched-chain amine and fraction No. 2 mainly comprising a straight-chain amine. Fraction No. 1 contained 38.9 wt % of the straight-chain amine, whereas Fraction No. 2 contained 99.3 wt % of the straight-chain amine.

A glass reaction vessel was charged with 58.8 g of Fraction No. 1, 15.6 g of water, 0.18 g of sodium bicarbonate 0.18 g of sodium pyrophosphate decahydrate, and 52.1 g of an aqueous solution of amine oxide (oxide concentration: 28.6 wt %) that had been prepared by oxidizing undistilled N,N-dimethylundecylamine as in Comparative Example 2. While the mixture was held at 80° C. under agitation, 67.2 g of aqueous 9.3 wt % hydrogen peroxide was added dropwise over a period of 1.5 hours, followed by the dropwise addition of another 9.3 wt % aqueous $H_2O_2$ over a period of 3 hours. After completion of the addition of $H_2O_2$, the reaction was continued for another 4 hours at 80° C. On the third hour of the continued reaction, 7.5 g of 35 wt % aqueous hydrogen peroxide was added to the reaction mixture. The conversion of the straight-chain amine was 100%, whereas the conversion of the branched-chain amine was 99.6 mol %. The level of residual hydrogen peroxide was 1.86 wt %.

Subsequently, a mixture of 40.9 g of Fraction No. 2, 6.6 g of 35 wt % aqueous hydrogen peroxide, 73.6 g of water, 0.13 g of sodium bicarbonate and 0.13 g of sodium pyrophosphate decahydrate was charged into the reaction vessel, and the second-stage reaction was effected at 80° C. for 8 hours. The overall conversion of the amines added in the first and second stages of the reaction had reached 99.6 mol %. The level of residual hydrogen peroxide was 0.095 wt %.

EXAMPLE 3

The procedure of Example 1 was repeated except that neither sodium bicarbonate nor sodium pyrophosphate decahydrate was added. In the first-stage reaction, 35 wt % aqueous hydrogen peroxide was added to the reaction mixture in amounts of 7.8 g and 6.5 g on the second and sixth hours, respectively, after the completion of the dropwise addition of 9.3 wt % aqueous $H_2O_2$. The conversions of the straight-chain and branched-chain amines on the eighth hour of the reaction that followed the addition of 9.3 wt % aqueous $H_2O_2$ were respectively 100% and 99.3 mol %. The level of residual hydrogen peroxide was 1.27 wt %.

The second-stage reaction was continued for 12 hours. Just before starting the reaction, 11.2 g of 35 wt % aqueous $H_2O_2$ was added to the reaction mixture. On the sixth, ninth and tenth hours of the reaction, 35 wt % aqueous $H_2O_2$ was also added in respective amounts of 2.0 g, 0.7 g and 0.16 g. The overall conversion of the amines added in the first- and second-stage reactions was 99.1 mol %, and the concentration of residual hydrogen peroxide was 0.098 wt %.

EXAMPLE 4

The procedure of Example 1 was repeated except that no aqueous amine oxide solution was added. In the first-stage reaction, 35 wt % aqueous hydrogen peroxide was added to the reaction mixture in amounts of 3.5 g and 3.7 g on the second and fourth hours, respectively, after the completion of the dropwise addition of 9.3 wt % aqueous $H_2O_2$. The conversions of the straight-chain and branched-chain amines on the tenth hour of the reaction that followed the addition of 9.3 wt % aqueous $H_2O_2$ were respectively 100% and 99.5 mol %. The level of residual hydrogen peroxide was 1.73 wt %.

The second-stage reaction was continued for 8 hours. Just before starting the reaction, 6.9 g of 35 wt % aqueous $H_2O_2$ was added to the reaction mixture. On the fourth and sixth hours of the reaction, 35 wt % aqueous $H_2O_2$ was also added in respective amounts of 1.0 g and 0.5 g. The overall conversion of the amines added in the first- and second-stage reactions was 99.2 mol %, and the concentration of residual hydrogen peroxide was 0.08 wt %.

What is claimed is:

1. In a process for producing an aqueous solution of a mixture of a straight-chain alkyl tertiary amine oxide and a branched-chain alkyl tertiary amine oxide by reacting aliphatic tertiary amines with an aqueous solution of hydrogen peroxide, the improvement comprising reacting a tertiary amine containing a major portion of a branched-chain alkyl tertiary amine and a minor portion of a straight-chain alkyl tertiary amine with an excess amount of hydrogen peroxide, so that at least 1 weight % of residual hydrogen peroxide is present after the oxidation of the branched-chain alkyl tertiary amine has been completed, and then, adding a straight-chain alkyl tertiary amine which is substantially free of a branched-chain alkyl group to the reaction mixture for permitting further reaction with hydrogen peroxide, wherein an amine conversion of at least 99 mol % is obtained.

2. A process according to claim 1 wherein said straight-chain alkyl tertiary amine is an aliphatic tertiary amine of the formula:

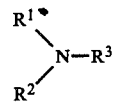

(wherein $R^1$ and $R^2$ independently represent methyl or ethyl group; $R^3$ is a straight-chain alkyl group having 8 to 18 carbon atoms).

3. A process according to claim 1 wherein said branched-chain alkyl tertiary amine is an aliphatic tertiary amine of the formula:

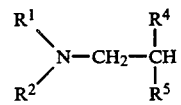

(wherein $R^1$ and $R^2$ independently represent methyl or ethyl group; $R^4$ and $R^5$ are each a straight-chain alkyl group, provided that the total number of carbon atoms in $R^4$ and $R^5$ is 6~16).

4. A process according to any one of the preceding claims wherein the branched-chain alkyl tertiary amine is oxidized in a dispersed phase in the presence of an amine oxide.

* * * * *